United States Patent
Gibbons et al.

(10) Patent No.: US 12,161,628 B2
(45) Date of Patent: Dec. 10, 2024

(54) COMBINATION THERAPY

(71) Applicants: Medivation Prostate Therapeutics LLC, New York, NY (US); Astellas Pharma Inc., Tokyo (JP)

(72) Inventors: Jacqueline Gibbons, San Francisco, CA (US); Joyce Mordenti, San Francisco, CA (US); Michiel De Vries, Leiden (NL); Walter Krauwinkel, Leiden (NL); Taoufik Ouatas, Bizerte (TN)

(73) Assignees: Medivation Prostate Therapeutics LLC, New York, NY (US); Astellas Pharma Inc., Tokyo (JP)

( * ) Notice: Subject to any disclaimer, the term of this patent is extended or adjusted under 35 U.S.C. 154(b) by 196 days.

(21) Appl. No.: 17/959,350

(22) Filed: Oct. 4, 2022

(65) Prior Publication Data

US 2023/0042959 A1 Feb. 9, 2023

Related U.S. Application Data

(63) Continuation of application No. 17/706,788, filed on Mar. 29, 2022, now abandoned, which is a continuation of application No. 15/751,542, filed as application No. PCT/US2016/046476 on Aug. 11, 2016, now abandoned.

(60) Provisional application No. 62/204,954, filed on Aug. 13, 2015, provisional application No. 62/204,281, filed on Aug. 12, 2015.

(51) Int. Cl.
| | |
|---|---|
| *A61K 31/4166* | (2006.01) |
| *A61K 31/438* | (2006.01) |
| *A61K 31/496* | (2006.01) |
| *A61K 31/515* | (2006.01) |
| *A61K 31/55* | (2006.01) |
| *A61K 45/06* | (2006.01) |
| *A61P 35/00* | (2006.01) |
| *A61K 31/435* | (2006.01) |

(52) U.S. Cl.
CPC ........ *A61K 31/4166* (2013.01); *A61K 31/438* (2013.01); *A61K 31/496* (2013.01); *A61K 31/515* (2013.01); *A61K 31/55* (2013.01); *A61K 45/06* (2013.01); *A61P 35/00* (2018.01); *A61K 31/435* (2013.01); *A61K 2300/00* (2013.01)

(58) Field of Classification Search
CPC ................. A61K 31/416; A61K 31/4166
See application file for complete search history.

(56) References Cited

U.S. PATENT DOCUMENTS

2018/0228790 A1 8/2018 Gibbons et al.

FOREIGN PATENT DOCUMENTS

WO 2017027660 A1 2/2017

OTHER PUBLICATIONS

Xtandi European Medicines Agency Committee for Medicinal Products for Human Use (CHMP) assessment report, Apr. 24, 2013, available at https://www.ema.europa.eu/en/documents/assessment-report/xtandi-epar-public-assessment-report_en.pdf.*
Ramadan et al., Enzalutamide for patients with metastatic castration-resistant prostate cancer, OncoTargets and Therapy 2015:8 871-876.*
Hamilton et al., The effect of rifampicin, a prototypical CYP3A4 inducer, on erlotinib pharmacokinetics in healthy subjects, Cancer Chemother Pharmacol. Mar. 2014;73(3):613-21, Epub Jan. 29, 2014.*
FDA Draft Guidance for Industry, "Drug Interaction Studies—Study Design, Data Analysis, Implications for Dosing and Labeling Recommendations", Feb. 2012.*
XTANDI® (enzalutamide) Summary Review, posted on FDA website Sep. 12, 2012.*
Scher et al., Antitumour activity of MDV3100 in castration-resistant prostate cancer: a phase 1-2 study, Lancet. Apr. 24, 2010; 375(9724): 1437-1446.*
Ex parte Richard Ditzik, Appeal 2018-00087, U.S. Appl. No. 14/169,232, U.S. Pat. No. 7,103,380, PTAB, Jul. 10, 2018, available at https://www.uspto.gov/sites/default/files/documents/fd2018-000087%20Ex%20parte%20Ditzik.pdf.*
Brief for Respondents in Opposition, *Vanda Pharmaceuticals Inc., v. Teva Pharmaceuticals USA, Inc.*, Dkt. No. 23-768, Mar. 18, 2024, available at https://assets.law360news.com/1816000/1816416/brief.pdf.*
McDonnell & Dang, "Basic Review of the Cytochrome P450 System," J. Adv. Pract. Oncol. 4, 263-68, 2013.
Nassr et al., "Effects of rifampicin on the pharmacokinetics of roflumilast and roflumilast N-oxide in healthy subjects," Br. J. Clin. Pharmacol. 68, 580-87, 2009.
NDA 203415, Clinical Information Amendment, Jun. 2015, 7 pages.
Nguyen et al., "Pharmacokinetic (PK) Drug Interaction Studies of Cabozantinib: Effect of CYP3A Inducer Rifampin and Inhibitor Ketoconazole on Cabozantinib Plasma PK and Effect of Cabozantinib on CYP2C8 Probe Substrate Rosiglitazone Plasma PK," J. Clin. Pharmacol. 55, 1012-23, 2015.
Noonan et al., "Clinical Activity of Abiraterone Acetate in Patients with Metastatic Castration-Resistant Prostate Cancer Progressing After Enzalutamide," 24 Annals of Oncol. 1802-07, 2013.
Obach et al., "In vitro cytochrome P450 inhibition data and the prediction of drug-drug interactions: qualitative relationships, quantitative predictions, and the rank-order approach," Clin Pharmacol Ther. 78, 582-92, 2005.
Obach et al., "The Utility of in Vitro Cytochrome P450 Inhibition Data in the Prediction of Drug-Drug Interactions," J Pharmacol Exp Ther. 316, 336-48, 2006, Epub Sep. 28, 2005.
Ohno et al., "General framework for the prediction of oral drug interactions caused by CYP3A4 induction from in vivo information," Clin. Pharmacokinet. 47, 669-80, 2008.

(Continued)

*Primary Examiner* — Svetlana M Ivanova
(74) *Attorney, Agent, or Firm* — Banner & Witcoff, Ltd.

(57) ABSTRACT

This disclosure provides a dosage regimen for co-administration of enzalutamide and a strong CYP3A4 inducer.

6 Claims, 11 Drawing Sheets

(56) References Cited

OTHER PUBLICATIONS

Ohno et al., "General framework for the quantitative prediction of CYP3A4-mediated oral drug interactions based on the AUC increase by coadministration of standard drugs," Clin. Pharmacokinet. 46, 681-96, 2007, abstract, 2 pages.
Peltoniemi, "Effects of Cytochrome P450 Enzyme Inhibitors and Inducers on the Metabolism of S-Ketamine," thesis submitted to University of Turku, 2013, 78 pages.
Poondru et al., email string dated Jul. 27, 2015, 2 pages.
Post Approval Study 1918-1, Cover letter submitting final report, Nov. 7, 2013, 1 page.
Post Approval Study 1918-1, Final Report, Jun. 20, 2013, 78 pages.
Prueksaritanont et al., "Drug-Drug Interaction Studies: Regulatory Guidance and an Industry Perspective," The AAPS Journal 15, 629-45, 2013.
Ramadan et al., "Enzalutamide for patients with metastatic castration-resistant prostate cancer," OncoTargets and Therapy 8, 871-76, 2015.
RAPAMUNE®, US Prescribing Information, Nov. 2015.
Rathkopf et al., "Phase I Dose-Escalation Study of the Novel Antiandrogen BMS-641988 in Patients with Castration-Resistant Prostate Cancer," 17(4) Clin. Cancer Res. 880-87, 2011.
Rathkopf et al., "Phase I Study of ARN-509, a Novel Antiandrogen, in the Treatment of Castration-Resistant Prostate Cancer," J. Clin. Oncol. 31, 3526-30, 2013.
*Roxane Laboratories, Inc. v. Vanda Pharmaceuticals*, 216 WL 5226531 (PTAB 2016).
Scher et al., "Antitumour activity of MDV3100 in castration-resistant prostate cancer: a phase 1-2 study," The Lancet 375, 1437-46, 2010.
Scher et al., "Increased Survival with Enzalutamide in Prostate Cancer after Chemotherapy," 367(13) N. Eng. J. Med. 1187-97, 2012.
Scher et al., Supplementary Appendix to "Increased Survival with Enzalutamide in Prostate Cancer after Chemotherapy," 367(13) N. Eng. J. Med. 1187-97, 2012.
Smith et al., "Effects of ketoconazole and carbamazepine on lapatinib parmacokinetics in healthy subjects," British Journal of Clinical Pharmacology 67, 421-26, 2009.
Spigset & Molden, "Cytochrome P-450 3A4—the most important arena for drug interactions in the body," Database Medline abstract accession No. NLM19092951, 1 page.
Srinivas, "Pharmacokinetic Interaction of Rifampicin with Oral Versus Intravenous Anticancer Drugs: Challenges, Dilemmas and Paradoxical Effects Due to Multiple Mechanisms," Drugs in R&D 16, 141-48, 2016.
Supplemental New Drug Application Approval Letter, Oct. 1, 2015, 4 pages.
Takeda et al., "Predicing drug-drug interactions through drug structural similarities and interaction networks incorporating pharmacokinetics and pharmacodynamics knowledge," J. Cheminform. 9, 9 pages, 2017.
TARCEVA® (erlotinib) prescribing information, Apr. 2015, 18 pages.
*Teva Pharms. USA, Inc. v. Corcept Therapeutics*, 18 F. 4th 1377, 1381 (Fed. Cir. 2021).
Tompkins & Wallace, "Mechanisms of Cytochrome P450 Induction," J. Biochem. Mol. Toxicol. 21(4), 176-81, 2007.
Townsend et al., "Pharmacokinetic Evaluation of CYP3A4-Mediated Drug-Drug Interactions of Isavuconazole With Rifampin, Ketoconazole, Midazolam, and Ethinyl Estradiol/Norethindrone in Healthy Adults," Clinical Pharmacology in Drug Development 6, 44-53, 2016.
Van Soest et al., "Cross-Resistance Between Taxanes and New Hormonal Agents Abiraterone and Enzalutamide May Affect Drug Sequence Choices in Metastatic Castration-Resistant Prostate Cancer," 49 Eur. J. Cancer 3821-30, 2013.
Waters, "Evaluation of drug-drug interactions for oncology therapies: in vitro-in vivo extrapolation model-based risk assessment," Br. J. Clin. Pharmacol. 79, 946-58, published online Dec. 1, 2014.
Wenning et al., "Effect of Rifampin, a Potent Inducer of Drug-Metabolizing Enzymes, on the Pharmacokinetics of Raltegravir," Antimicrobial Agents and Chemotherapy 53, 2852-56, 2009.
Written Opinion for PCT/US2016/046476, 8 pages, mailed Nov. 3, 2016.
Wu et al., "Text Mining for Drug-Drug Interaction," Methods Mol. Biol. 1159, 47-75, 2014.
XALKORI®, US Prescribing Information, Sep. 2015.
XTANDI® (enzalutamide) Approval Letter posted on FDA website Sep. 12, 2012, 8 pages.
XTANDI® (enzalutamide) Product Monograph (Canada), initial approval date May 28, 2013, revised Jan. 14, 2019, 52 pages.
XTANDI® (enzalutamide) Screenshot list of publicly available documents in drug approval package, 1 page, website created Sep. 12, 2012.
XTANDI® (enzalutamide) Summary Review, posted on FDA website Sep. 12, 2012, 15 pages.
XTANDI® (enzalutamide) Tablet Prescribing Information (Japan), initial approval date Mar. 24, 2014, revised Feb. 2018, 6 pages.
XTANDI® (enzalutamide) US Prescribing Information, 16 pages, Aug. 2012.
XTANDI® (enzalutamide) US Prescribing Information, Jul. 2015, 22 pages.
XTANDI® (enzalutamide) US Prescribing Information, Aug. 2015, 19 pages.
XTANDI® (enzalutamide) US Prescribing Information, Oct. 2015, 21 pages.
Yang et al., "Effect of rifampin on the pharmacokinetics, safety and tolerability of navitoclax (ABT-263), a dual inhibitor pf Bcl-2 and Bcl-XL, in patients with cancer," Journal of Clinical Pharmacy and Therapeutics 39, 680-84, 2014.
Yu et al., "Drug Disposition and Drug-Drug Interaction Data in 2013 FDA New Drug Applications: A Systematic Review," Drug Metab. Dispos. 42, 1991-2001, 2014.
Yu et al., "Risk of Clinically Relevant Pharmacokinetic-Based Drug-Drug Interactions with Drugs Approved by the U.S. Food and Drug Administration Between 2013 and 2016,", Drug Metab. Dispos. 46(6), 835-45, 2018.
Zhang et al., "Predicting Drug-Drug Interactions: An FDA Perspective," The AAPS Journal 11, 300-06, 2009.
Zhou, "Drugs Behave as Substrates, Inhibitors and Inducers of Human Cytochrome P450 3A4," Current Drug Metabolism 9, 310-22, 2008.
TAXOTERE® US Prescribing Information, 2014.
Ai et al., "In silico methods for predicting drug-drug interactions with cytochrome P-450s, transporters and beyond," Adv. Drug Deliv. Rev. 86, 46-60, 2015, abstract, 2 pages.
Almond et al., "Prediction of Drug-Drug Interactions Arising from CYP3A Induction Using a Physiologically Based Dynamic Model," Drug Metab. Dispos. 44, 821-32, 2016.
Anonymous, "Drug Interactions Flockhart TableTM," Indiana University, drug-interactions.medicine.iu.edu/Main-Table.aspx, downloaded Apr. 2019, 6 pages.
Anonymous, "Impact Story: Supporting Drug Development Through Physiologically Based Pharmacokinetic Modeling," fda.gov/drugs/science-research-drugs/impact-story-supporting-drug-development-through-physiologically-based-pharmacokinetic-modeling, downloaded Apr. 29, 2019, 7 pages.
Anonymous, "Rifadin (rifampin) dose, indications, adverse effects, interactions," downloaded from PDR.net, Apr. 25, 2019, 36 pages.
Anonymous, FDA Drug Development and Drug Interactions, Table of Substrates, Inhibitors and Inducers (2020).
Balcazar, email dated Jul. 27, 2015, and attachment, 24 pages.
Barrus, email dated Jul. 30, 2015, 1 page.
Baxter, ed., Stockley's Drug Interactions, Chapter 1 ("General considerations and an outline survey of some basic interaction mechanisms"), pp. 1-11, Pharmaceutical Press, Chicago, 8th edition, 2008.
Baxter, ed., Stockley's Drug Interactions, Index pp. 1431-1432, Pharmaceutical Press, Chicago, 8th edition, 2008.

(56) References Cited

OTHER PUBLICATIONS

Benoist et al., "Pharmacokinetic Aspects of the Two Novel Oral Drugs Used for Metastatic Castration-Resistant Prostate Cancer: Abiraterone Acetate and Enzalutamide," Clin. Pharmacokinet. 55, 1369-80, 2016.
Bolt et al., "Interaction of Rifampicin Treatment with Pharmacokinetics and Metabolism of Ethinyloestradiol in Man," Acta Endocrinologica, 85, 189-197, 1977.
Bolt, "Interactions between Clinically Used Drugs and Oral Contraceptives," Environmental Health Perspectives, 102 (Suppl.9), 35-38, 1994.
BOSULIF® prescribing information, Sep. 2012, 13 pages.
BOSULIF® US Prescribing Information, Nov. 2014.
Caterina et al., "Pharmacokinetic drug-drug interaction and their implication in clinical management," J. Res. Med. Sci. 18, 601-10, 2013.
Chen & Raymond, "Roles of rifampicin in drug-drug interactions: underlying molecular mechanisms involving the nuclear pregnane X receptor," Annals of Clinical Microbiology and Antimicrobials 5, 2006, 11 pages.
Clinical Overview, Clinical Pharmacology Update, Mar. 2015, 8 pages.
Clinical Study Report, "A Phase I, Randomized, Open-label, 2-arm Parallel-design Study to Determine the Effect of Multiple-dose Rifampin on the Pharmacokinetics, Safety and Tolerability of Single-dose Enzalutamide in Healthy Male Subjects," Sep. 23, 2014, 495 pages.
Denmeade & Issacs, "A History of Prostate Cancer Treatment," 2 Nature Reviews Cancer 389-96, 390-93, 2002.
Egelund et al., "Concomitant Use of Carbamazepine and Rifampin in a Patient With Mycobacterium avium Complex and Seizure Disorder," J. Pharmacy Technology 30, 93-96, 2014.
FDA Draft Guidance for Industry, "Clinical Drug Interaction Studies—Study Design, Data Analysis, and Clinical Implications," Feb. 2012, 79 pages.
FDA Draft Guidance for Industry, "Clinical Drug Interaction Studies—Study Design, Data Analysis, and Clinical Implications," Oct. 2017, 32 pages.
FDA Draft Guidance for Industry, "In Vitro Metabolism- and Transporter-Mediated Drug-Drug Interaction Studies," Oct. 2017, 47 pages.
Ferguson et al., "Human CYP2C8 is Transcriptionally Regulated by the Nuclear Receptors Constitutive Androstane Receptor, Pregnane X Receptor, Glucocorticoid Receptor, and Hepatic Nuclear Factor 4alpha," Mol. Pharmacol. 68(3), 747-57, 2005.
Finch et al., "Rifampin and Rifabutin Drug Interactions," Arch. Intern. Med. 162, 985-92, 2002.
Fowler et al., "Progress in Prediction and Interpretation of Clinically Relevant Metabolic Drug-Drug Interactions: a Minireview Illustrating Recent Developments and Current Opportunities," Curr. Pharmacol. Rep. 3, 36-49, 2017.
Gavai et al., "Chapter 6: Novel Androgen Receptor Antagonists for the Treatment of Prostate Cancer, in Accounts" in Drug Discovery: Case Studies in Medical Chemistry 120 (Barrish et al. eds., 2011.
Gibbons et al., "Clinical Pharmacokinetic Studies of Enzalutamide," Clin. Pharmacokinet. 54, 1043-55, 2015.
Gibbons et al., "Pharmacokinetic Drug Interaction Studies with Enzalutamide," Clin. Pharmacokinet. 54, 1057-69, 2015.
Gibbons et al., Nonfinal Office Action and initialed IDS for U.S. Appl. No. 15/751,610, filed Jun. 25, 2018, 12 pages.
Gibbons et al., U.S. Appl. No. 16/231,632, filed Dec. 24, 2018, 4 pages.
Gibbons et al., U.S. Appl. No. 17/979,063, filed Nov. 2, 2022.
Gibbons, email dated Jul. 30, 2015, 1 page.
Glass et al., "Patient Demographics, Quality of Life, and Disease Features of Men with Newly Diagnosed Prostate Cancer: Trends in the PSA Era," 82(1) J. Urology 60-66, 62, 2013.
Gottlieb et al., "INDI: a computational framework for inferring drug interactions and their associated recommendations," Molecular Systems Biology 8, Article 592, 2012, 12 pages.
Guengerich, "Oxidation of 17alpha-Ethynylestradiol by Human Liver Cytochrome P-450," Mol. Pharmacol. 33, 500-508, 1988.
Guthrie et al., "The Rising Tide of Polypharmacy and Drug-Drug Interactions: Population Database Analysis 1995-2010," 13(74) BMC Medicine 1-10, 2015.
Hachad et al., "A useful tool for drug interaction evaluation: The University of Washington Metabolism and Transport Drug Interaction Database," Human Genomics 5, 61-72, 2010.
Hamilton et al., "The effect of rifampicin, a prototypical CYP3A4 inducer, on erlotinib pharmacokinetics in healthy subjects," Cancer Chemother. Pharmacol. 73, 613-21, 2014.
Huang, "New Era in Drug Interaction Evaluation: US Food and Drug Administration Update on CYP Enzymes, Transporters, and the Guidance Process," J. Clin. Pharmacol. 48, 662-670, 2008.
IMBRUVICA®, US Prescribing Information, Jan. 2015.
International Search Report for PCT/US2016/046476, 5 pages, mailed Oct. 28, 2016.
Kenny et al., "Considerations from the Innovation and Quality Induction Working Group in Response to Drug-Drug Interaction Guidances from Regulatory Agencies: Focus on CYP3A4 mRNA In Vitro Response Thresholds, Variability, and Clinical Relevance," Drug Metab. Dispos. 46, 1285-303, Sep. 2018.
Kroiss et al., "Drug interactions with mitotane by induction of CYP3A4 metabolism in the clinical management of adrenocortical carcinoma," Clin. Endocrinol. 75, 585-91, 2011.
Leibowitz-Amit & Joshua, "Targeting the androgen receptor in the management of castration-resistant prostate cancer: rationale, progress, and future directions," Curr. Oncol. 19, S22-31, 2012.
Li et al., "Differential Metabolism of Gefitinib and Erlotinib by Human Cytochrome P450 Enzymes," Clin. Cancer Res. 13, 3731-37, 2007.
Loriot et al., "Antitumour Activity of Abiraterone Acetate Against Metastatic Castration-Resistant Prostate Cancer Progressing After Docetaxel and Enzalutamide (MDV3100)," 24(7) Annnals of Oncol. 1807-12, 1810, 2013.
Loue & Tod, "Reliability and Extension of Quantitative Prediction of CYP3A4-Mediated Drug Interactions Based on Clinical Data," The AAPS Journal 16, 1309-20, 2014.
McClain, "The Significance of Hepatic Microsomal Enzyme Induction and Altered Thyroid Function in Rats: Implications for Thyroid Gland Neoplasia," Toxicologic Pathology 17, 294-306, 1989.
Center for Drug Evaluation and Research, Application No. 203415Orig1s000 (Xtandi) Clinical Pharmacology and Biopharmaceutics Review(s), Aug. 31, 2012.
Diaz et al., "Patients' Perception of Cancer-Related Fatigue: Results of a Survey to Assess the Impact on their Everyday Life," Clin. Transl. Oncol. 10, 753-57, 2009.
Esper et al., "Measuring Quality of Life in Men with Prostate Cancer Using the Functional Assessment of Cancer Therapy—Prostate Instrument," Urology 50(6), 920-28, 1997.
Storey et al., "Clinically Relevant Fatigue in Men with Hormone-Sensitive Prostate Cancer on Long-Term Androgen Deprivation Therapy," Annals of Oncol. 23, 1542-49, 2012.
Weiss et al., "Impact of enzalutamide and its main metabolite N-desmethyl enzalutamide on pharmacokinetically important drug metabolizing enzymes and drug transporters," Biopharm. Drug Dispos. 38, 517-25, 2017.

* cited by examiner

PK parameters ($C_{max}$ and $AUC_{0-inf}$) are for enzalutamide plus N-desmethyl enzalutamide, except in the food-effect trial, where they are for enzalutamide alone.

COMBINATION THERAPY

This application is a continuation of Ser. No. 17/706,788 filed Mar. 29, 2022, which is a continuation of Ser. No. 15/751,542 filed Feb. 9, 2018, which is a US national phase application of PCT/US2016/046476 filed Aug. 11, 2016 and which claims priority to and incorporates by reference U.S. provisional application Ser. No. 62/204,281, filed on Aug. 12, 2015, and U.S. provisional application Ser. No. 62/204,954 filed on Aug. 13, 2015.

Each reference cited in this disclosure is incorporated herein in its entirety.

TECHNICAL FIELD

This disclosure relates generally to cancer treatment.

BRIEF DESCRIPTION OF THE DRAWINGS

FIG. 2A, linear. FIG. 2B, semi-log scale plot.

FIG. 3A, linear. FIG. 3B, semi-log scale plot.

FIG. 4A, linear. FIG. 4B, semi-log scale plot.

FIG. 5A, linear. FIG. 5B, semi-log scale plot.

DETAILED DESCRIPTION

Figure 1:
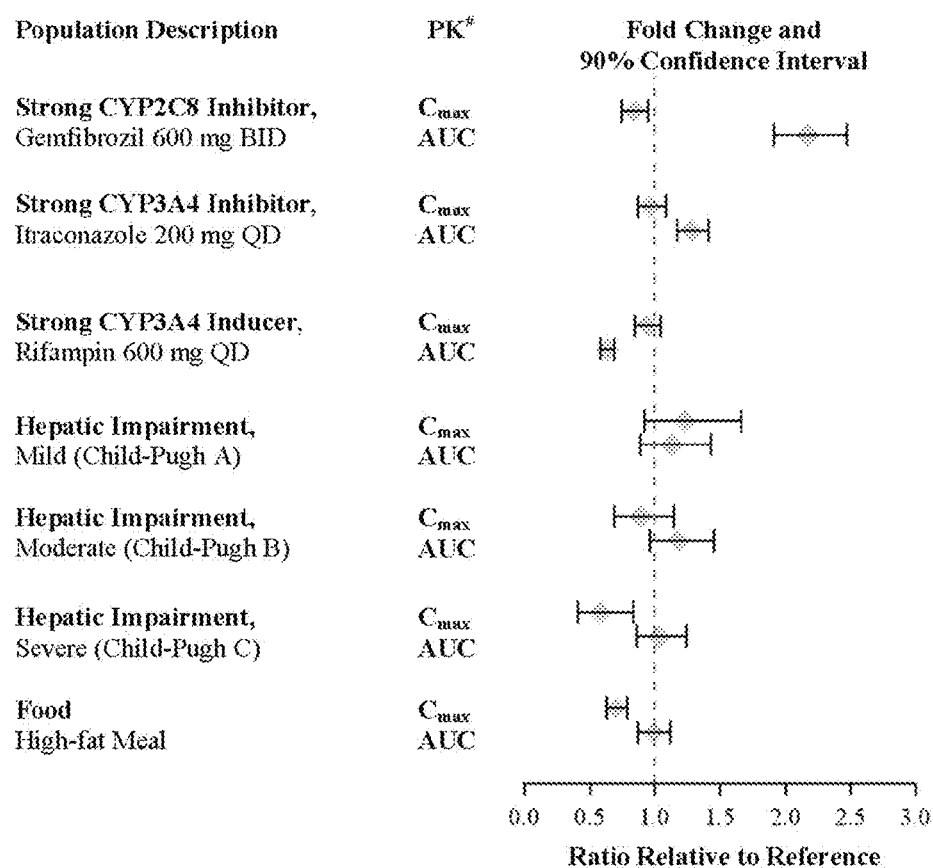
FIG. 1 shows the effects of rifampin (as well as other drugs and intrinsic/extrinsic factors) on the pharmacokinetic parameters $C_{max}$ and $AUC_{0-inf}$ for enzalutamide and its major active metabolite N-desmethyl enzalutamide.

Enzalutamide, 4-{3-[4-cyano-3-(trifluoromethyl)phenyl]-5,5-dimethyl-4-oxo-2-sulfanylideneimidazolidin-1-yl}-2-fluoro-N-methylbenzamide (e.g., XTANDI®), is an androgen receptor inhibitor and can be used to treat cancers such as prostate cancers, breast cancers, and ovarian cancers. Enzalutamide is also a strong CYP3A4 inducer in humans; at steady state, enzalutamide reduces the plasma exposure to the CYP3A4 substrate midazolam. There are, however, situations in which co-administration of enzalutamide with a strong CYP3A4 inducer (e.g., carbamazepine, phenobarbital, phenytoin, rifabutin, rifampin, rifapentine) are nevertheless desirable or cannot be avoided. In a drug-drug interaction trial in healthy volunteers, a single 160 mg oral dose of XTANDI® was administered alone or after multiple oral doses of rifampin (strong CYP3A4 and moderate CYP2C8 inducer). Rifampin decreased the $AUC_{0-inf}$ of enzalutamide and its major active metabolite N-desmethyl enzalutamide by 37% with no effect on $C_{max}$. The results are summarized in FIG. 1. Thus, in which co-administration of enzalutamide with a strong CYP3A4 inducer (e.g., carbamazepine, phenobarbital, phenytoin, rifabutin, rifampin, rifapentine) are desirable or cannot be avoided, the daily dose of enzalutamide may be increased from, e.g., 160 mg/day to 200-300 mg/day (e.g., 200, 205, 210, 215, 220, 225, 230, 235, 240, 245, 250, 255, 260, 265, 270, 275, 280, 285, 290, 295, 300 mg/day).

"Co-administration" of enzalutamide and a strong CYP3A4 inducer means administration in any manner in which the pharmacological effects of enzalutamide and the strong CYP3A4 inducer overlap in the patient at the same time. Co-administration does not require that both agents be administered in a single pharmaceutical composition, in the same dosage form, by the same route of administration, or for the same length of time.

Enzalutamide is typically formulated for oral administration. Formulations of enzalutamide are disclosed, e.g., in the prescribing information for XTANDI®, and in US 2014/0378517, US 2014/0179749, and US 2014/0100256.

Patients who can be treated with the disclosed co-administration regimes include patients with prostate cancer (including metastatic prostate cancer, castration-resistant prostate cancer, hormone-sensitive prostate cancer, metastatic castration-resistant prostate cancer, metastatic hormone-sensitive prostate cancer), breast cancer (including triple-negative breast cancer), and ovarian cancer. Prostate cancer patients who can be treated using the disclosed co-administration regimes include patients with metastatic castration-resistant prostate cancer (CRPC) who had previously received chemotherapy (e.g., docetaxel) as well as patients with CRPC who are chemotherapy-naïve.

The following example illustrates but does not limit the scope of the appended claims.

Example 1. Pharmacokinetics

Data handling. The actual sampling time of enzalutamide and its metabolites for 6 subjects (7 samples in total), and the actual sampling time of the 2-hour rifampin sample of subject 10002 on Day 21 deviated more than 10% of the scheduled time point. Therefore, the concentrations from these samples were excluded from the summary statistics, but were included in the calculation of the pharmacokinetic parameters.

Enzalutamide and its Metabolites M1 (Inactive) and M2 (Active)

Figure 2A:
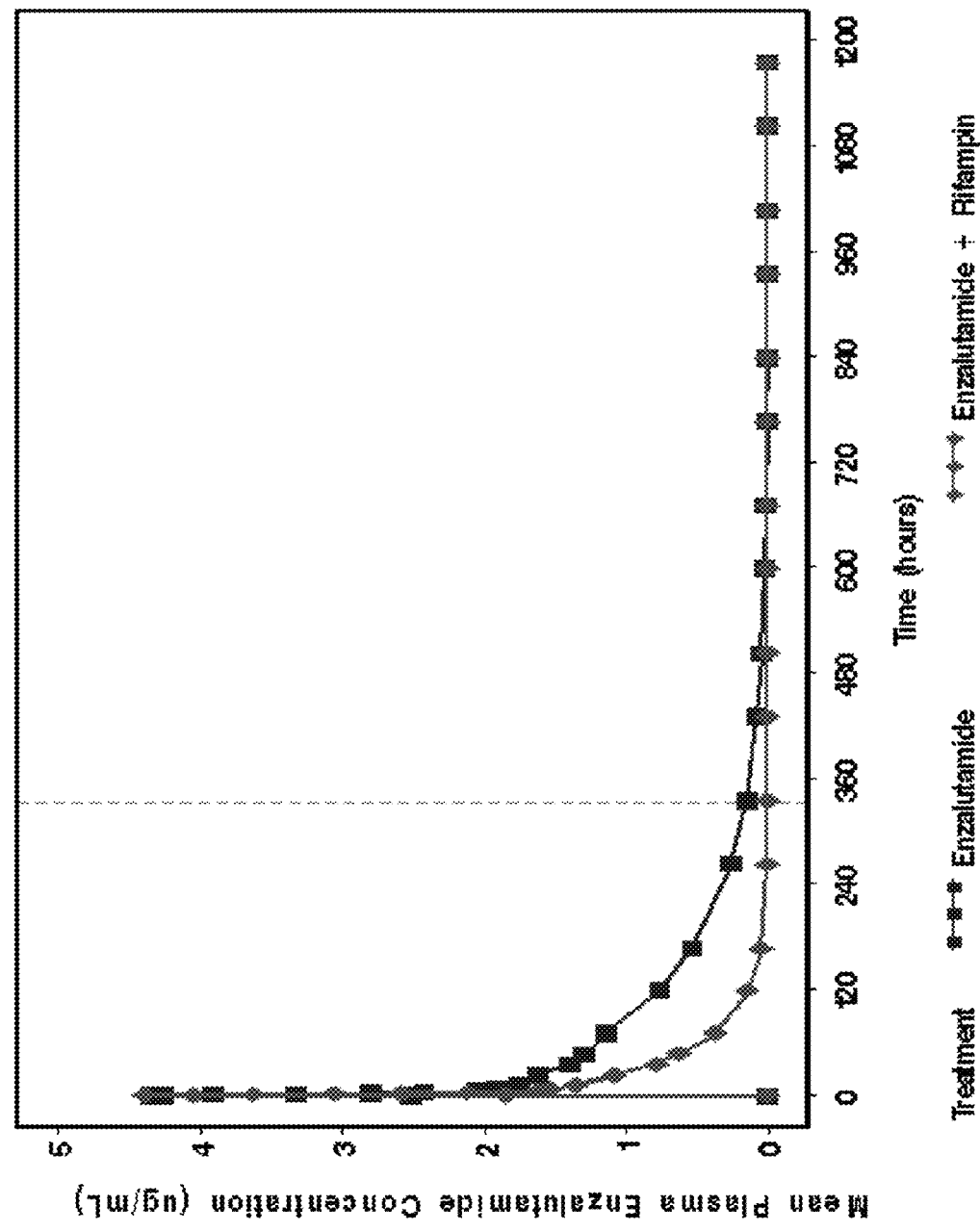
FIGS. 2A-B. Graphs showing mean plasma enzalutamide concentrations after a single dose of 160 mg enzalutamide alone or in the presence of multiple doses of 600 mg rifampin once daily. The vertical line at 336 h signifies the end of rifampin treatment.
Figure 2B:
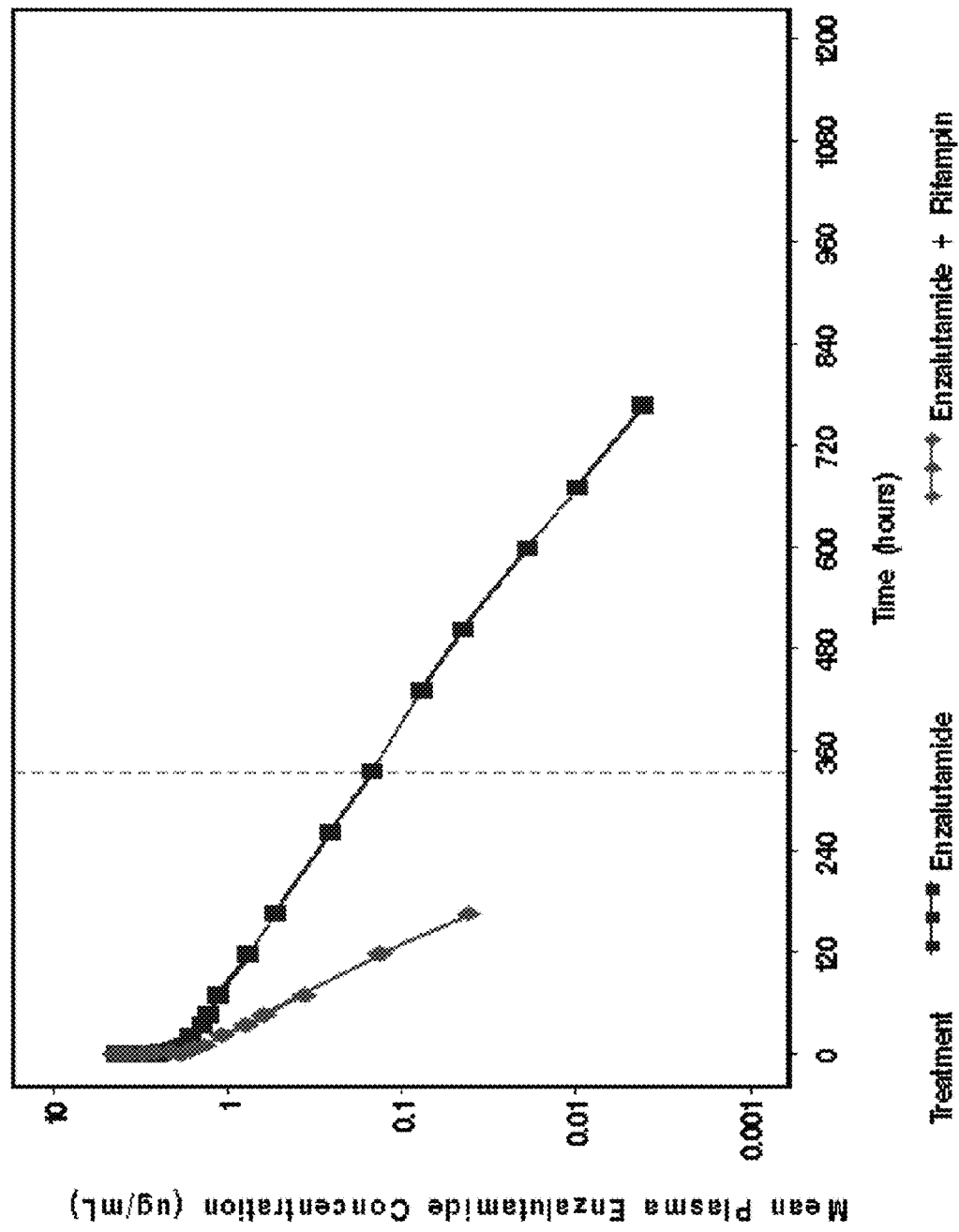

Mean enzalutamide plasma concentrations versus time profiles (linear and semi-logarithmic) are presented in FIG. 2. Summary statistics of enzalutamide pharmacokinetic parameters are shown in Table 1. In Table 2, the statistical assessments of the effect of rifampin on enzalutamide after a single dose of enzalutamide are presented.

As indicated in the semi-logarithmic concentrations versus time profiles, elimination of enzalutamide was faster in the presence of rifampin compared to after administration of enzalutamide alone. For all subjects in the rifampin treatment arm, the last quantifiable enzalutamide concentration was measured prior to the end of the rifampin dosing period (up to 13 days after enzalutamide dosing). Therefore, it was deemed appropriate to calculate $AUC_{inf}$, $t_{1/2}$, CL/F and $V_z/F$ using non-compartmental methods. % AUC was low and individual values ranged between 0.658% and 4.56%.

In the presence of rifampin, enzalutamide $AUC_{0-336hr}$ and $AUC_{inf}$ were 63% (geometric mean ratio [GMR]:36.79; 90% CI:33.36-40.57) and 66% (GMR:33.76 (90% CI:30.31-37.60) lower, respectively, compared to enzalutamide alone. $C_{max}$ was not significantly changed (GMR:93.03; 90% CI:83.67-103.45), and similar mean $t_{max}$ values were observed (i.e., 1.039 hours versus 1.078 hours), with the comparable ranges of individual values.

Mean $t_{1/2}$ was shorter when enzalutamide was given in the in the presence of rifampin (30.70 h) compared to enzalutamide alone (90.10 hours). Mean apparent clearance was higher in the presence of rifampin (1.856 L/h) compared to enzalutamide alone (0.6330 L/h), while the apparent volume of distribution ($V_z/F$) did not change.

Between subject variation in enzalutamide $AUC_{0-336hr}$, $AUC_{inf}$ and $C_{max}$ was low and was not influenced by the presence of rifampin, with values ranging between 13.2% and 19.4%.

mary statistics of M1 pharmacokinetic parameters are shown in Table 3. In Table 4, the statistical results of the effect of rifampin on M1 after a single dose of enzalutamide are presented.

Based on the mean concentration-time profiles, the maximum M1 plasma concentrations were comparable between treatments; however, the maximum plasma concentration was reached somewhat earlier in the presence of rifampin. Elimination of M1 was faster in the presence of rifampin, though the elimination of M1 did not change after discontinuation of rifampin at t=336 hours.

In the presence of rifampin, M1 $AUC_{0-336hr}$ and AUCs were 15% (GMR:84.94; 90% CI: 69.07-104.46) and 32% (GMR:67.53; 90% CI:44.56-102.33) lower, respectively compared to enzalutamide alone. The 90% CI of the GMRs for both parameters were wide. It should be noted that AUCs could only be accurately determined for 4 subjects in the enzalutamide treatment arm (treatment arm 1) and 6 subjects in the enzalutamide+rifampin treatment arm (treatment arm

TABLE 1

Summary Statistics of Plasma Enzalutamide Pharmacokinetic Parameters After Single Dose Administration of 160 mg Enzalutamide Alone or in the Presence of Multiple Doses of 600 mg Rifampin Once Daily

| Parameter | n | Mean | SD (CV %) | Min | Median | Max |
|---|---|---|---|---|---|---|
| Enzalutamide | | | | | | |
| $AUC_{0-336\,h}$ (µg · h/mL) | 14 | 239.2 | 41.06 (17.2) | 179 | 233.0 | 320 |
| $AUC_{0-t}$ (µg · h/mL) | 14 | 257.7 | 50.35 (19.5) | 187 | 253.7 | 336 |
| $AUC_{inf}$ (µg · h/mL) | 14 | 262.0 | 50.91 (19.4) | 191 | 259.0 | 341 |
| $C_{max}$ (µg/mL) | 14 | 4.931 | 0.8196 (16.6) | 3.10 | 5.140 | 5.94 |
| $t_{max}$ (h) | 14 | 1.078 | 0.4804 (NA) | 0.500 | 0.9100 | 2.00 |
| $t_{1/2}$ (h) | 14 | 90.10 | 27.25 (30.2) | 35.5 | 85.69 | 142 |
| CL/F (L/h) | 14 | 0.6330 | 0.1259 (19.9) | 0.470 | 0.6184 | 0.840 |
| $V_z/F$ (L) | 14 | 79.82 | 21.68 (27.2) | 41.1 | 78.11 | 123 |
| Enzalutamide + Rifampin (Test) | | | | | | |
| $AUC_{0-336\,h}$ (µg · h/mL) | 14 | 87.50 | 11.55 (13.2) | 71.8 | 84.80 | 109 |
| $AUC_{0-t}$ (µg · h/mL) | 14 | 85.41 | 10.99 (12.9) | 69.3 | 82.67 | 105 |
| $AUC_{inf}$ (µg · h/mL) | 14 | 87.58 | 11.68 (13.3) | 72.0 | 84.75 | 110 |
| $C_{max}$ (µg/mL) | 14 | 4.567 | 0.6435 (14.1) | 3.20 | 4.560 | 5.70 |
| $t_{max}$ (h) | 14 | 1.039 | 0.3497 (NA) | 0.500 | 1.000 | 2.00 |
| $t_{1/2}$ (h) | 14 | 30.70 | 6.162 (20.1) | 17.7 | 31.80 | 39.4 |
| CL/F (L/h) | 14 | 1.856 | 0.2350 (12.7) | 1.46 | 1.888 | 2.22 |
| $V_z/F$ (L) | 14 | 81.59 | 17.45 (21.4) | 52.0 | 80.49 | 119 |

CV %: coefficient of variation expressed as percentage;
Max: maximum;
Min: minimum;
NA: not applicable

TABLE 2

Statistical Assessment of the Effect of Multiple Doses of Rifampin on Exposure Parameters of Plasma Enzalutamide After Single Dose Administration of 160 mg Enzalutamide

| Parameter (Units) | Geometric LS Means | | Ratio (%) (Test/Reference) | 90% CI (%) |
|---|---|---|---|---|
| | Enzalutamide (Reference) | Enzalutamide + Rifampin (Test) | | |
| n | 14 | 14 | | |
| $AUC_{0-336h}$ (µg · h/mL) | 236.0 | 86.82 | 36.79 | 33.36-40.57 |
| $AUC_{inf}$ (µg · h/mL) | 257.4 | 86.89 | 33.76 | 30.31-37.60 |
| $C_{max}$ (µg/mL) | 4.862 | 4.523 | 93.03 | 83.67-103.45 |

LS: Least squares

Enzalutamide Metabolite M1

Figure 3A:
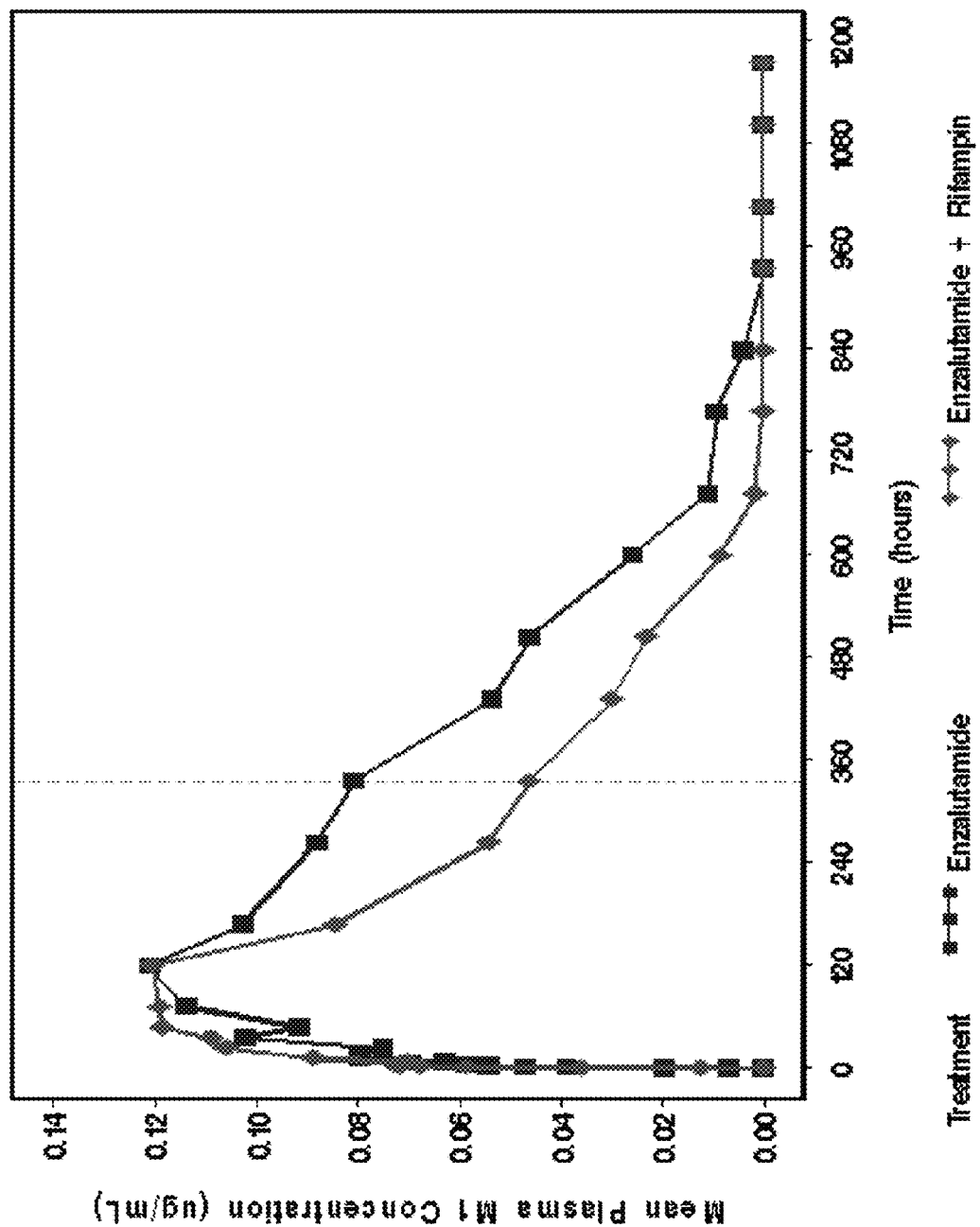
FIGS. 3A-B. Graphs showing mean plasma M1 concentrations after a single dose of 160 mg enzalutamide alone or in the presence of multiple doses of 600 mg rifampin once daily. The vertical line at 336 h signifies the end of rifampin treatment.
Figure 3B:
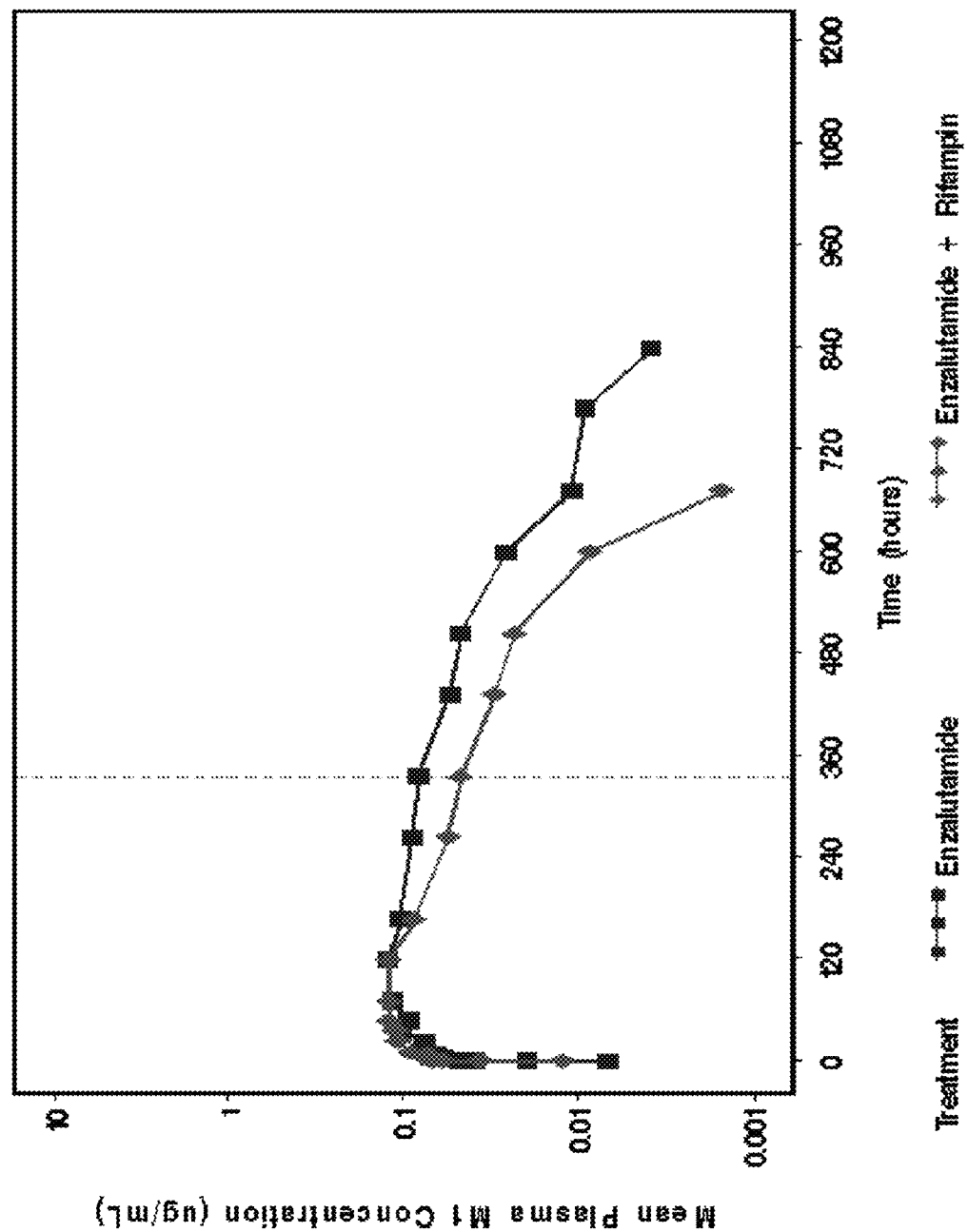

Mean M1 plasma concentrations versus time profiles (linear and semi-logarithmic) are presented in FIG. 3. Sum- 2). For $AUC_{inf}$ values for which the percentage extrapolated (% AUC) were higher than 20%, the $AUC_{inf}$ was excluded from the statistical analysis. Mean M1 $t_{1/2}$ was somewhat shorter in the presence of rifampin (194.5 hours) compared to enzalutamide alone (223.9 hours).

$C_{max}$ appeared to be similar (GMR:96.56; 90% CI:77.68-120.02); however, median $t_{max}$ was reached earlier in the presence of rifampin (58.21 hours) compared to after administration of enzalutamide alone (109.6 hours), with smaller ranges of individual values in the presence of rifampin.

M1 MPRs, molecular weight corrected and based on $AUC_1$, were higher in the presence of rifampin compared to enzalutamide alone, with mean values of 0.4897 (range: 0.210 to 0.809) and 0.2165 (range: 0.152 to 0.314), respectively.

Between subject variation in M1 $AUC_{0-336hr}$, $AUC_{inf}$ and $C_{max}$ was moderate and was not influenced by the presence of rifampin, with values ranging between 27.5% and 47.3%.

Based on the mean concentration-time profiles, maximum M2 plasma concentrations were higher and were reached earlier in the presence of rifampin compared to enzalutamide alone. Elimination of M2 was slightly faster in the presence of rifampin. The elimination of M2 did not change after discontinuation of rifampin at t=336 hours.

In the presence of rifampin, M2 $AUC_{0-336hr}$ was 15% higher (GMR:114.8; 90% CI:103.49-127.34), while $AUC_{inf}$ was 15% lower (GMR:84.74 (90% CI:77.13-93.11) compared to enzalutamide alone. % AUC was low and ranged between 1.25% and 5.79%. Mean M2 $t_{1/2}$ was somewhat shorter in the presence of rifampin (154.7 hours) compared to enzalutamide alone (190.4 h). M2 $C_{max}$ was 34% higher (GMR:133.7; 90% CI:118.63-150.76), and median $t_{max}$ was reached earlier (i.e., 71.86 hours versus 167.7 hours).

TABLE 3

Summary Statistics of Plasma M1 Pharmacokinetic Parameters After Single Dose Administration of 160 mg Enzalutamide Alone or in the Presence of Multiple Doses of 600 mg Rifampin Once Daily

| Parameter | n | Mean | SD (CV %) | Min | Median | Max |
|---|---|---|---|---|---|---|
| Enzalutamide | | | | | | |
| $AUC_{0-336\,h}$ (μg · h/mL) | 14 | 32.49 | 8.930 (27.5) | 20.3 | 31.38 | 54.5 |
| $AUC_{0-t}$ (μg · h/mL) | 14 | 47.87 | 16.73 (35.0) | 25.9 | 46.66 | 92.4 |
| $AUC_{inf}$ (μg · h/mL) | 8 | 62.14 | 19.84 (31.9) | 38.2 | 57.39 | 102 |
| $C_{max}$ (μg/mL) | 14 | 0.1414 | 0.04662 (33.0) | 0.0761 | 0.1350 | 0.238 |
| $t_{max}$ (h) | 14 | 109.6 | 74.5 (NA) | 36.0 | 119.1 | 263 |
| $t_{1/2}$ (h) | 12 | 223.9 | 62.85 (28.1) | 86.2 | 236.6 | 303 |
| MPR (MWC) | 12 | 0.2233 | 0.05737 (25.7) | 0.157 | 0.2194 | 0.323 |
| Enzalutamide + Rifampin (Test) | | | | | | |
| $AUC_{0-336\,h}$ (μg · h/mL) | 14 | 28.35 | 9.840 (34.7) | 13.0 | 27.54 | 47.8 |
| $AUC_{0-t}$ (μg · h/mL) | 14 | 34.33 | 13.76 (40.1) | 13.0 | 34.59 | 64.5 |
| $AUC_{inf}$ (μg · h/mL) | 4 | 44.09 | 20.87 (47.3) | 22.3 | 42.40 | 69.3 |
| $C_{max}$ (μg/mL) | 14 | 0.1374 | 0.04751 (34.6) | 0.0724 | 0.1370 | 0.230 |
| $t_{max}$ (h) | 14 | 58.21 | 32.19 (NA) | 12.0 | 47.92 | 120 |
| $t_{1/2}$ (h) | 10 | 194.5 | 53.56 (27.5) | 131 | 183.2 | 274 |
| MPR (MWC) | 10 | 0.4894 | 0.2085 (42.6) | 0.217 | 0.4757 | 0.844 |

CV %: coefficient of variation expressed as percentage;
Max: maximum;
Min: minimum;
MPR (MWC): metabolite versus parent ratio (molecular weight corrected);
NA: not applicable

TABLE 4

Statistical Assessment of the Effect of Multiple Doses of Rifampin on Exposure Parameters of Plasma M1 After Single Dose Administration of 160 mg Enzalutamide

| | Enzalutamide (Reference) | | Enzalutamide + Rifampin (Test) | | Ratio (%) | |
|---|---|---|---|---|---|---|
| Parameter (Units) | n | Geometric LS Mean | n | Geometric LS Mean | (Test/Reference) | 90% CI (%) |
| $AUC_{0-336\,h}$ (μg · h/mL) | 14 | 31.43 | 14 | 26.70 | 84.94 | 69.07-104.46 |
| $AUC_{inf}$ (μg · h/mL) | 8 | 59.62 | 4 | 40.26 | 67.53 | 44.56-102.33 |
| $C_{max}$ (μg/mL) | 14 | 0.1346 | 14 | 0.1300 | 96.56 | 77.68-120.02 |

LS: Least Squares

Enzalutamide Metabolite M2

Figure 4A:
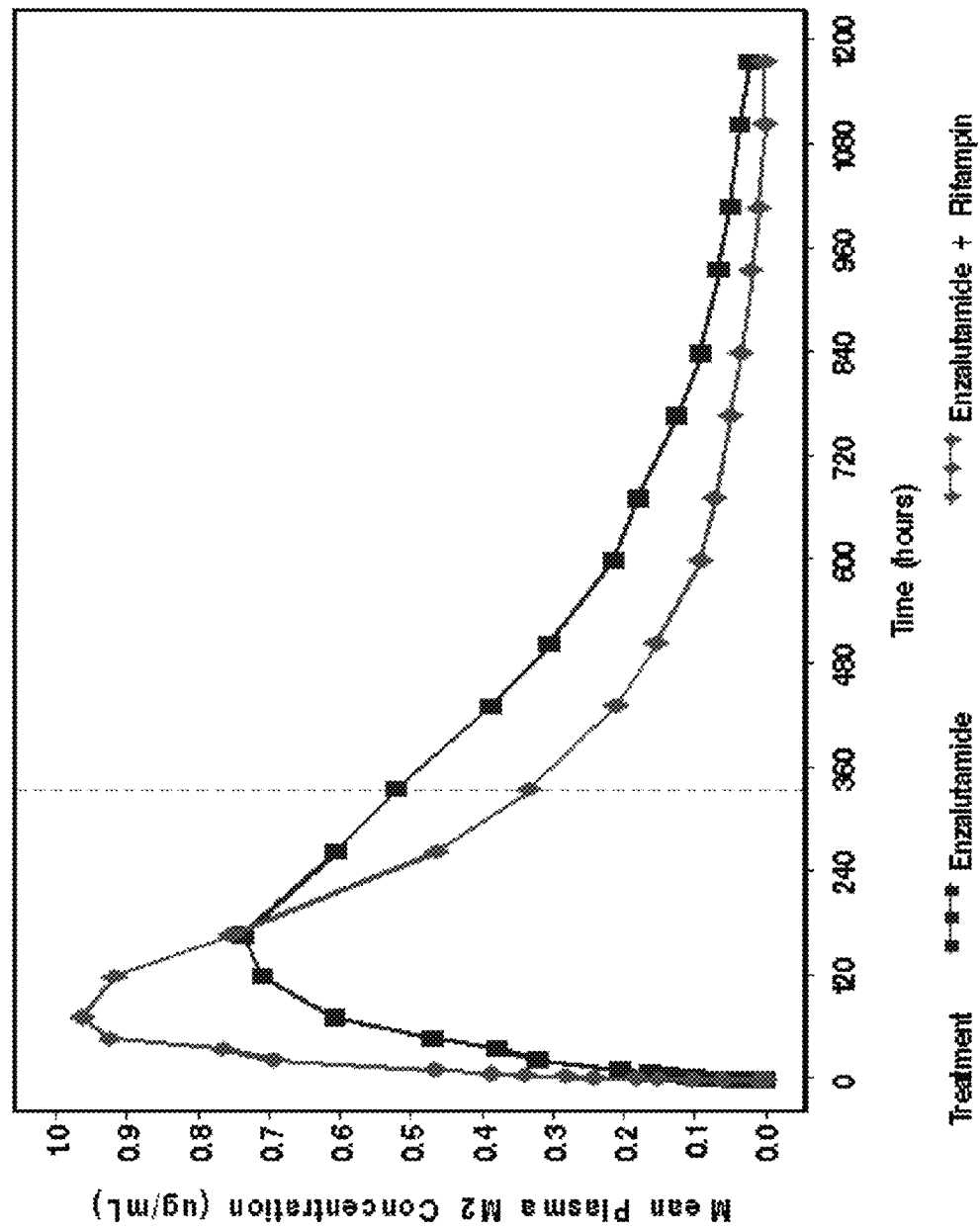
FIGS. 4A-B. Graphs showing mean plasma M2 concentrations after a single dose of 160 mg enzalutamide alone or in the presence of multiple doses of 600 mg rifampin once daily. The vertical line at 336 h signifies the end of rifampin treatment.
Figure 4B:
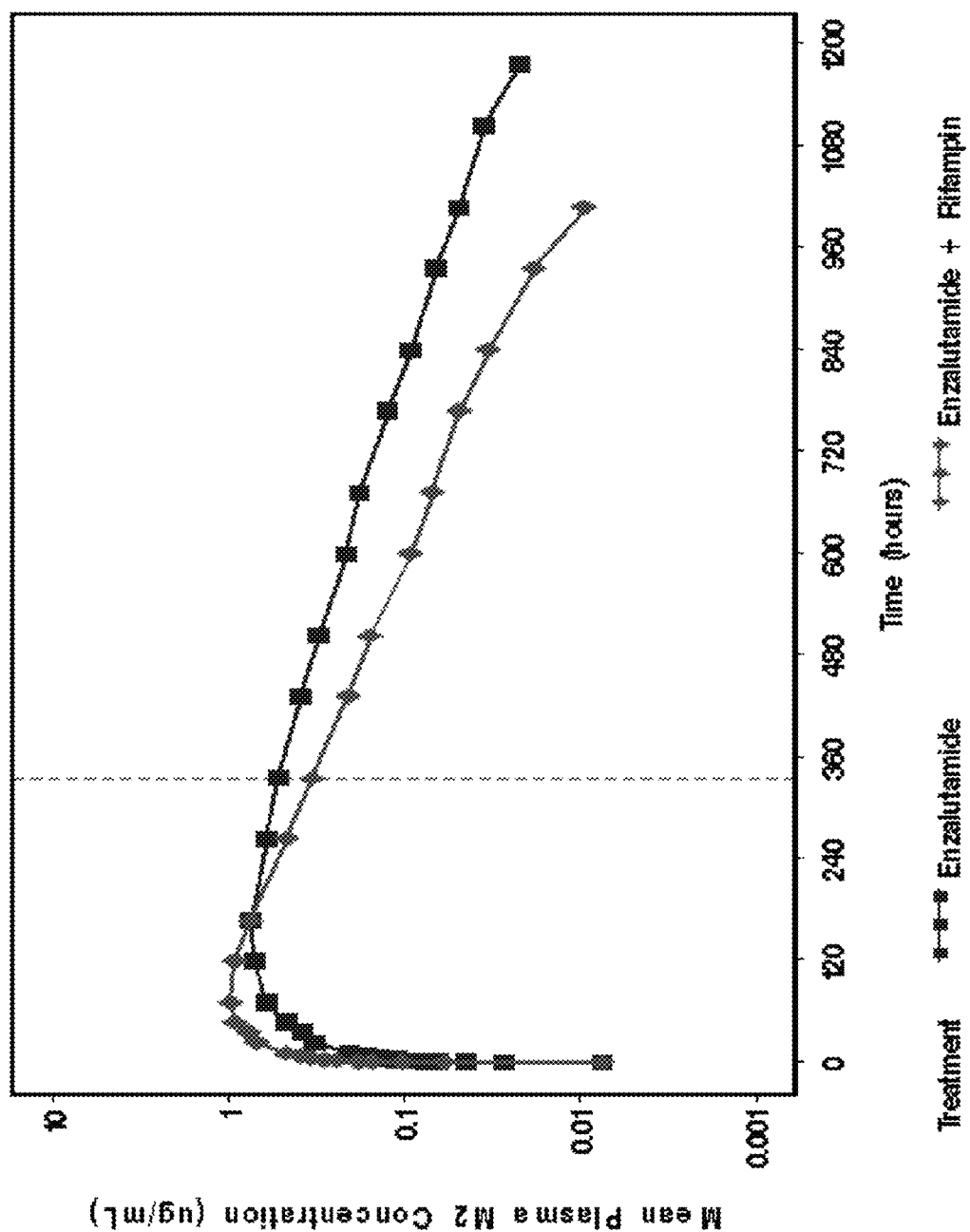

Mean M2 plasma concentrations versus time profiles (linear and semi-logarithmic) are presented in FIG. 4. Summary statistics of M2 pharmacokinetic parameters are shown in Table 5. In Table 6, the statistical results of the effect of rifampin on M2 after a single dose of enzalutamide are presented.

M2 MPR, molecular weight corrected and based on $AUC_{inf}$ was higher in the presence of rifampin compared to enzalutamide alone, with mean values of 3.443 (range: 2.71 to 4.33) and 1.385 (range: 1.04 to 2.08), respectively.

Between subject variation in M2 $AUC_{0-336hr}$, $AUC_{inf}$ and $C_{max}$ was low and was not influenced by the presence of rifampin, with values ranging between 11.0% and 20.8%.

TABLE 5

Summary Statistics of Plasma M2 Pharmacokinetic Parameters After Single Dose Administration of 160 mg Enzalutamide Alone or in the Presence of Multiple Doses of 600 mg Rifampin Once Daily

| Parameter | n | Mean | SD (CV %) | Min | Median | Max |
|---|---|---|---|---|---|---|
| Enzalutamide | | | | | | |
| $AUC_{0-336h}$ (µg·h/mL) | 14 | 197.6 | 41.15 (20.8) | 146 | 184.1 | 286 |
| $AUC_{0-t}$ (µg·h/mL) | 14 | 344.3 | 58.19 (16.9) | 249 | 338.3 | 440 |
| $AUC_{inf}$ (µg·h/mL) | 14 | 354.0 | 59.18 (16.7) | 255 | 351.0 | 451 |
| $C_{max}$ (µg/mL) | 14 | 0.7546 | 0.1778 (23.6) | 0.542 | 0.7145 | 1.18 |
| $t_{max}$ (h) | 14 | 161.3 | 37.00 (NA) | 120 | 167.7 | 265 |
| $t_{1/2}$ (h) | 14 | 190.4 | 31.07 (16.3) | 142 | 182.1 | 253 |
| MPR (MWC) | 14 | 1.431 | 0.3156 (22.1) | 1.07 | 1.373 | 2.15 |
| Enzalutamide + Rifampin (Test) | | | | | | |
| $AUC_{0-336h}$ (µg·h/mL) | 14 | 224.0 | 24.72 (11.0) | 173 | 221.9 | 263 |
| $AUC_{0-t}$ (µg·h/mL) | 14 | 292.1 | 33.51 (11.5) | 221 | 293.5 | 338 |
| $AUC_{inf}$ (µg·h/mL) | 14 | 297.9 | 33.52 (11.3) | 226 | 299.4 | 343 |
| $C_{max}$ (µg/mL) | 14 | 0.9949 | 0.1413 (14.2) | 0.743 | 1.010 | 1.29 |
| $t_{max}$ (h) | 14 | 66.75 | 19.23 (NA) | 47.9 | 71.86 | 120 |
| $t_{1/2}$ (h) | 14 | 154.7 | 18.58 (12.0) | 125 | 152.5 | 190 |
| MPR (MWC) | 14 | 3.558 | 0.5368 (15.1) | 2.81 | 3.372 | 4.47 |

CV %: coefficient of variation expressed as percentage;
Max: maximum;
Min: minimum;
MPR (MWC): metabolite versus parent ratio (molecular weight corrected);
NA: not applicable

TABLE 6

Statistical Assessment of the Effect of Multiple Doses of Rifampin on Exposure Parameters of Plasma M2 After Single Dose Administration of 160 mg Enzalutamide

| Parameter (Units) | Geometric LS Means | | Ratio (%) (Test/Reference) | 90% CI (%) |
|---|---|---|---|---|
| | Enzalutamide (Reference) | Enzalutamide + Rifampin (Test) | | |
| n | 14 | 14 | | |
| $AUC_{0-336h}$ (µg·h/mL) | 194.0 | 222.7 | 114.8 | 103.49-127.34 |
| $AUC_{inf}$ (µg·h/mL) | 349.3 | 296.0 | 84.74 | 77.13-93.11 |
| $C_{max}$ (µg/mL) | 0.7370 | 0.9856 | 133.7 | 118.63-150.76 |

LS: Least Squares

Sum of Enzalutamide Plus M2

Figure 5A:
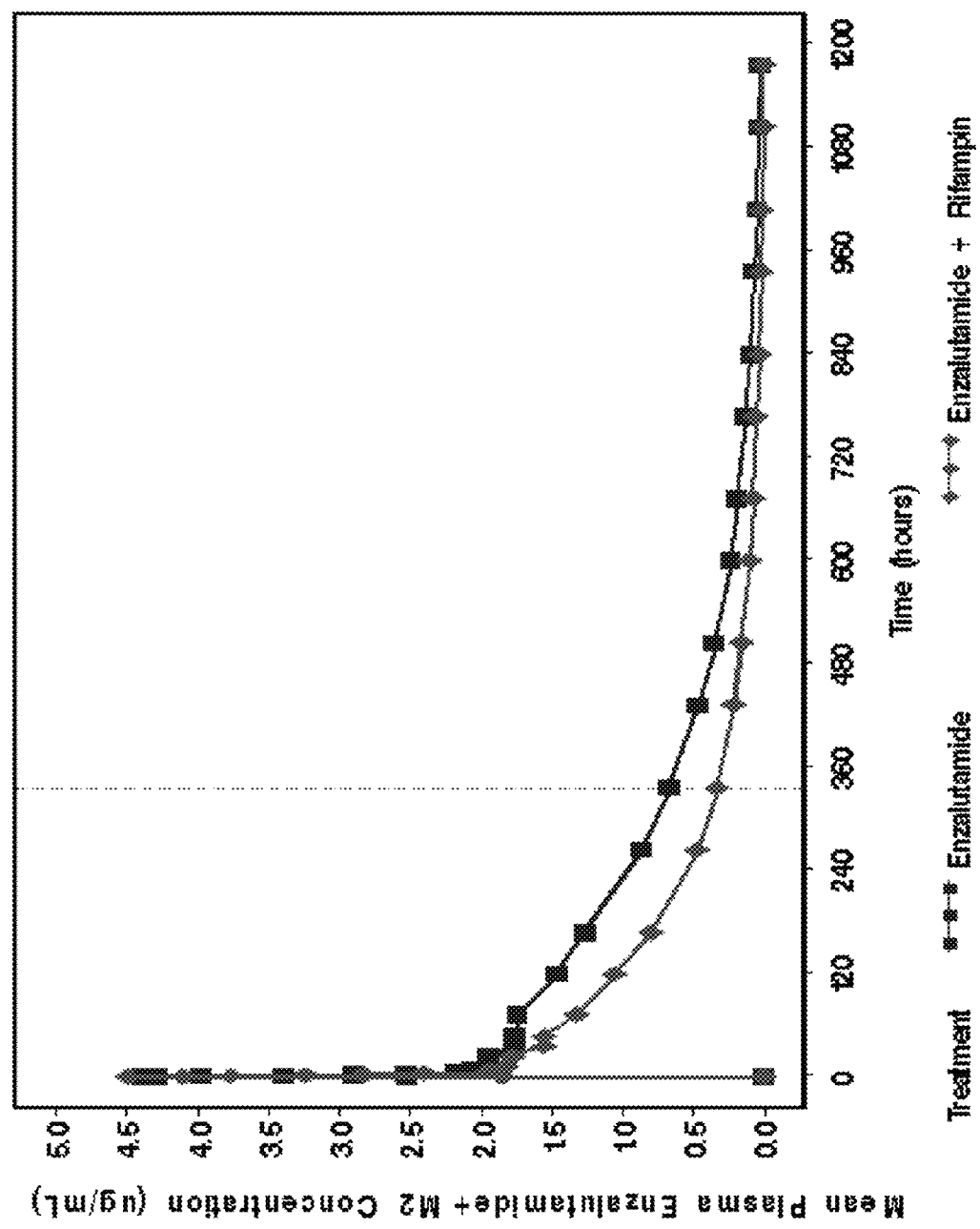
FIGS. 5A-B. Graphs showing mean plasma sum of enzalutamide plus M2 concentrations after a single dose of 160 mg enzalutamide alone or in the presence of multiple doses of 600 mg rifampin once daily. The vertical line at 336 h signifies the end of rifampin treatment.
Figure 5B:
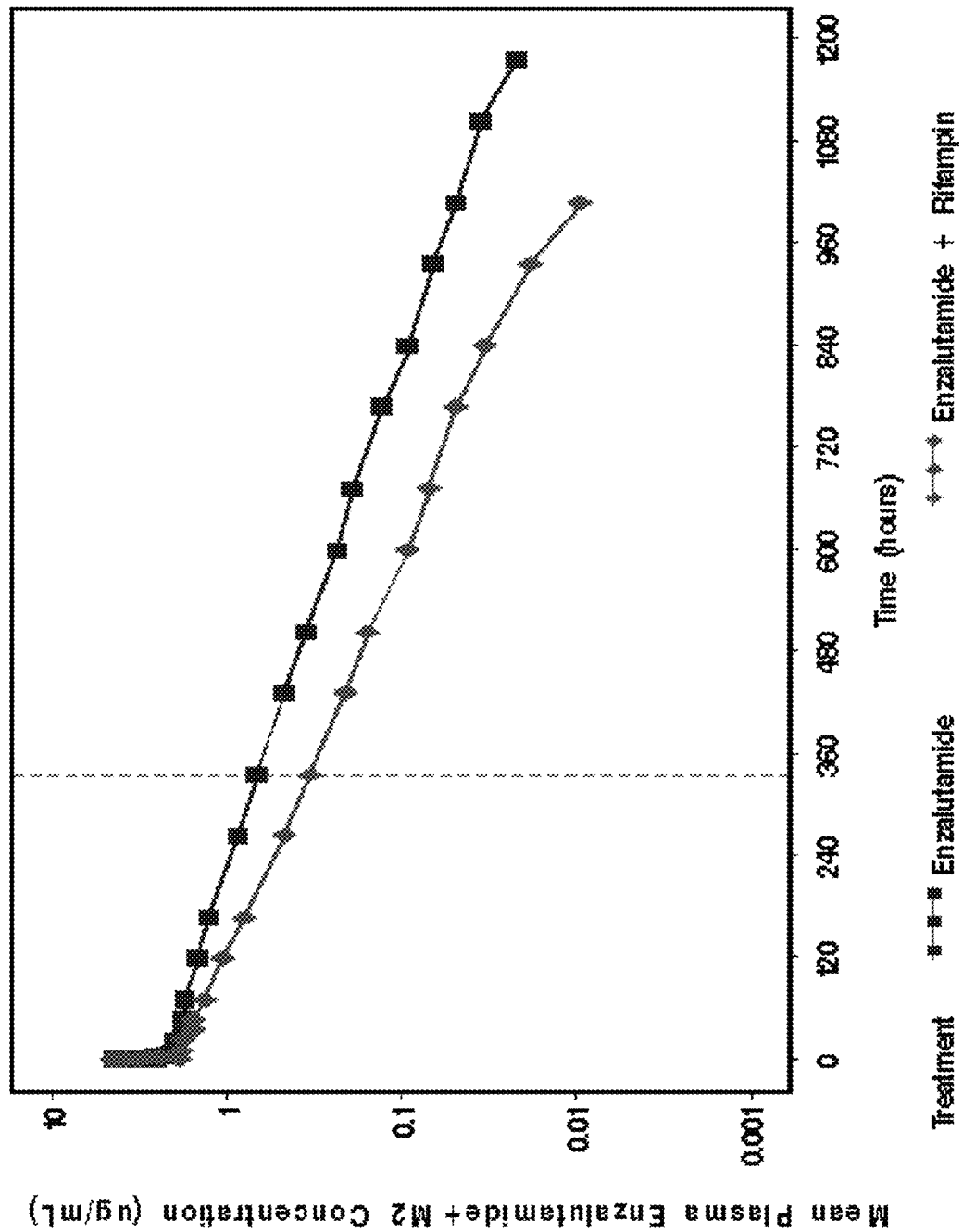

Mean sum of enzalutamide plus M2 plasma concentrations versus time profiles (linear and semi-logarithmic) are presented in FIG. 5. Summary statistics of the sum of enzalutamide plus M2 pharmacokinetic parameters are shown in Table 7. In Table 8, the statistical results of the effect of rifampin on the sum of enzalutamide plus M2 after a single dose of enzalutamide are presented.

Based on the mean concentration-time profiles, mean sum of enzalutamide plus M2 plasma concentrations were comparable between treatments up to roughly 48 hours after administration. Thereafter, plasma concentrations of the sum of enzalutamide plus M2 declined slightly faster in the presence of rifampin. After discontinuation of rifampin at t=336 hours, no change in decline was observed.

In the presence of rifampin, sum of enzalutamide plus M2 $AUC_{0-336hr}$ and AUCs were 28% (GMR:71.56; 90% CI:66.39-77.13) and 37% (GMR 63.26; 90% CI:58.17-68.79) lower, respectively, compared to enzalutamide alone. Mean $t_{1/2}$ was somewhat shorter in the presence of rifampin (149.4 hours) compared to enzalutamide alone (178.6 hours).

$C_{max}$ was comparable between treatments (GMR:94.32; 90% CI:85.05-104.60), and similar mean $t_{max}$ values were observed (i.e., 1.039 hours versus 1.078 hours) with the same ranges of individual values. Between subject variation in sum of enzalutamide plus M2 $AUC_{0-336hr}$, $AUC_{inf}$ and $C_{max}$ was low and was not influenced by presence of rifampin, with values ranging between 9.7% and 16.4%.

TABLE 7

Summary Statistics of Plasma Sum of Enzalutamide plus M2 Pharmacokinetic Parameters After Single Dose Administration of 160 mg Enzalutamide Alone or in the Presence of Multiple Doses of 600 mg Rifampin Once Daily

| Parameter | n | Mean | SD (CV %) | Min | Median | Max |
|---|---|---|---|---|---|---|
| Enzalutamide | | | | | | |
| $AUC_{0-336h}$ (µg · h/mL) | 14 | 436.9 | 59.33 (13.6) | 359 | 421.1 | 574 |
| $AUC_{0-t}$ (µg · h/mL) | 14 | 603.5 | 90.32 (15.0) | 466 | 604.9 | 774 |
| $AUC_{inf}$ (µg · h/mL) | 14 | 612.5 | 92.00 (15.0) | 472 | 614.5 | 779 |
| $C_{max}$ (µg/mL) | 14 | 4.980 | 0.8153 (16.4) | 3.16 | 5.192 | 5.97 |
| $t_{max}$ (h) | 14 | 1.078 | 0.4804 (NA) | 0.500 | 0.9100 | 2.00 |
| $t_{1/2}$ (h) | 14 | 178.6 | 29.04 (16.3) | 128 | 168.3 | 221 |
| Enzalutamide + Rifampin (Test) | | | | | | |
| $AUC_{0-336h}$ (µg · h/mL) | 14 | 311.5 | 30.34 (9.7) | 256 | 311.9 | 371 |
| $AUC_{0-t}$ (µg · h/mL) | 14 | 379.6 | 38.40 (10.1) | 304 | 384.9 | 445 |
| $AUC_{inf}$ (µg · h/mL) | 14 | 385.2 | 38.38 (10.0) | 309 | 390.8 | 450 |
| $C_{max}$ (µg/mL) | 14 | 4.674 | 0.6340 (13.6) | 3.33 | 4.665 | 5.80 |
| $t_{max}$ (h) | 14 | 1.039 | 0.3497 (NA) | 0.500 | 1.000 | 2.00 |
| $t_{1/2}$ (h) | 14 | 149.4 | 17.79 (11.9) | 119 | 148.5 | 179 |

CV %: coefficient of variation expressed as percentage;
Max: maximum;
Min: minimum;
NA: not applicable

TABLE 8

Statistical Assessment of the Effect of Multiple Doses of Rifampin on Exposure Parameters of Plasma Sum of Enzalutamide plus M2 After Single Dose Administration of 160 mg Enzalutamide

| | Geometric LS Means | | | |
|---|---|---|---|---|
| Parameter (Units) | Enzalutamide (Reference) | Enzalutamide + Rifampin (Test) | Ratio (%) (Test/Reference) | 90% CI (%) |
| n | 14 | 14 | | |
| $AUC_{0-336h}$ (µg · h/mL) | 433.3 | 310.1 | 71.56 | 66.39-77.13 |
| $AUC_{inf}$ (µg · h/mL) | 606.0 | 383.3 | 63.26 | 58.17-68.79 |
| $C_{max}$ (µg/mL) | 4.911 | 4.633 | 94.32 | 85.05-104.60 |

LS: Least Squares

Rifampin

Figure 6:
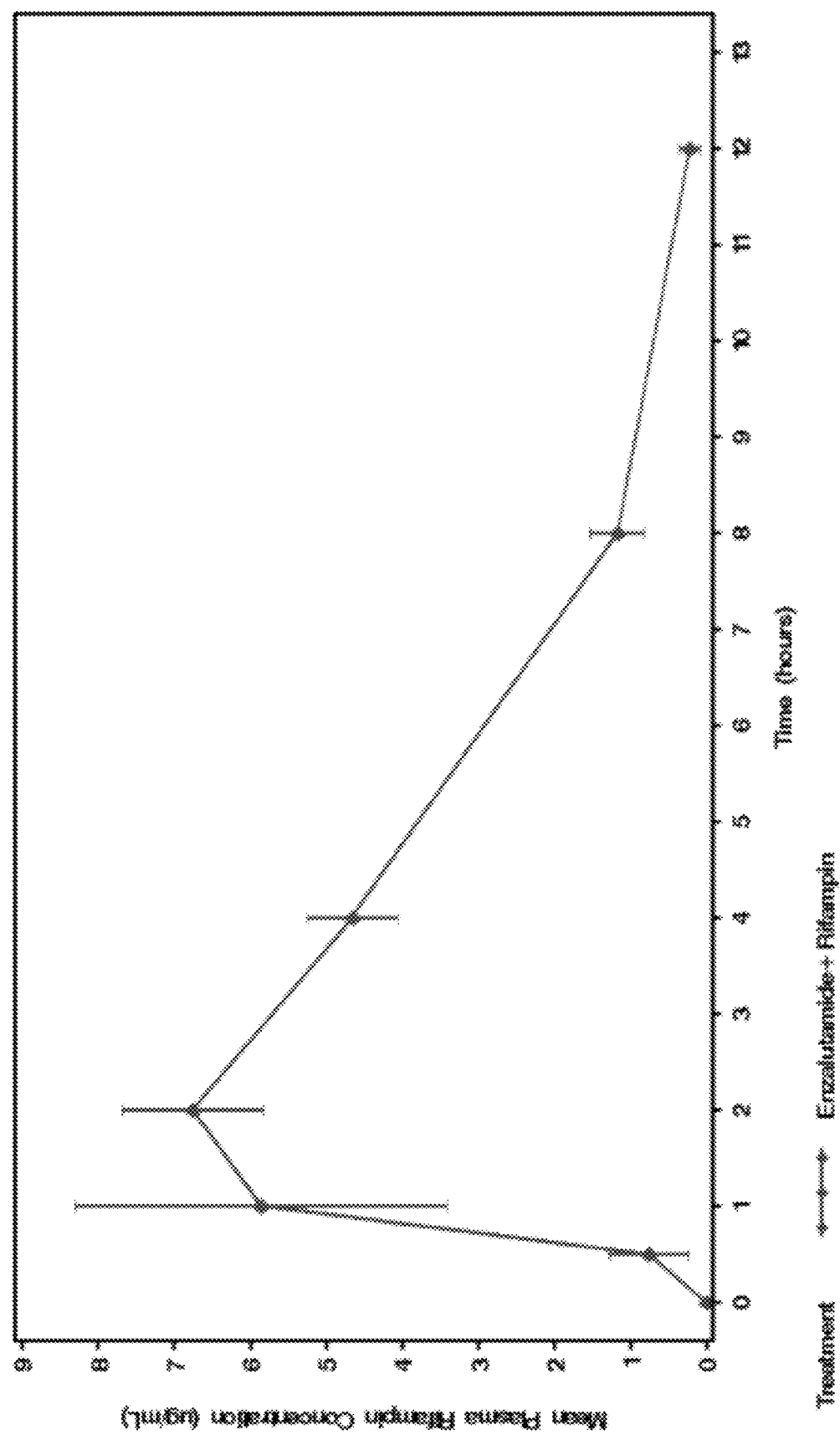
FIG. 6. Graph showing mean plasma concentration-time curve of rifampin on day 8 after multiple doses of 600 mg rifampin once daily.
Figure 7:
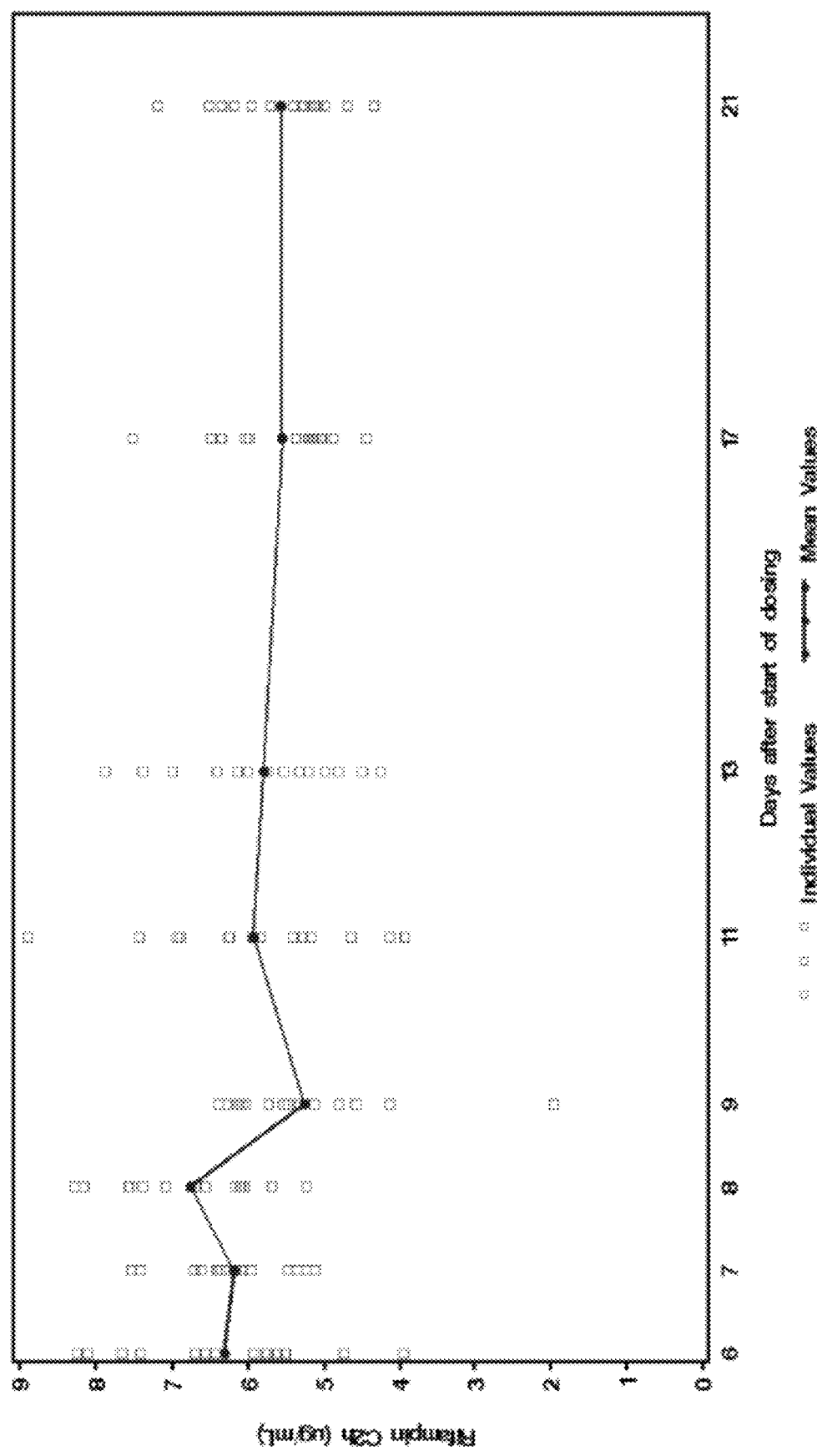
FIG. 7. Graph showing mean and individual $C_{2h}$ plasma concentrations of rifampin during multiple doses of 600 mg rifampin once daily for 21 days.

Mean rifampin plasma concentrations versus time profile during 1 dosing interval on day 8 is presented in FIG. 6. In FIG. 7, individual and mean rifampin $C_{2H}$ plasma concentrations that were obtained during the entire dosing period of 21 days are presented. Summary statistics of rifampin pharmacokinetic parameters are shown in Table 9.

Mean plasma rifampin concentrations on day 8 were in line with reported concentrations (Martin et al, 2011; Polk et al, 2001) indicating that relevant concentrations for CYP3A4 and CYP2C8 induction were likely reached by day 8. Median $t_{max}$ was reached 2 hours post-dose. $C_{2h}$ concentrations were generally consistent throughout the 21-day dosing period indicating that steady-state rifampin exposure was achieved prior to and maintained after administration of enzalutamide.

Intersubject variation in rifampin $C_{2H}$ was low with values ranging between 12.0% and 22.6%.

TABLE 9

Summary Statistics of Rifampin Pharmacokinetic Parameters After Multiple Doses of 600 mg Rifampin Once Daily Day 8

| Parameter | n | Mean | SD (CV %) | Min-Max | Median |
|---|---|---|---|---|---|
| $C_{min}$ (µg/mL) | 14 | 0 | NA (NA) | 0-0 | NA |
| $C_{2h}$ (µg/mL) | 14 | 6.759 | 0.9330 (13.8) | 5.24-8.27 | 6.625 |
| $C_{max}$ (µg/mL) | 14 | 7.163 | 1.222 (17.1) | 5.24-8.89 | 7.035 |
| $t_{max}$ (h) | 14 | 1.720 | 0.4700 (NA) | 1.00-2.00 | 2.000 |
| $AUC_{tau}$ | 14 | 35.59 | 4.450(12.5) | 28.3-46.4 | 35.25 |

CV %: coefficient of variation expressed as percentage; Max: maximum; Min: minimum; NA: not applicable

CONCLUSION

After administration of a 160 mg single enzalutamide dose in the presence of multiple doses of 600 mg rifampin once daily:

Enzalutamide $AUC_{inf}$ was 66% lower (GMR 33.76; 90% CI:30.31-37.60) compared to enzalutamide alone, while $C_{max}$ was comparable (GMR:93.03; 90% CI:83.67-103.45).

Mean $t_{max}$ values were similar (i.e., 1.039 hours versus 1.078 hours), with comparable ranges of individual values.

M1 $AUC_{0-336hr}$ and $AUC_{inf}$ were 15% (GMR:84.94; 90% CI:69.07-104.46) and 32% (GMR:67.53; 90% CI:44.56-102.33) lower, respectively, while $C_{max}$ appeared to be similar (GMR:96.56; 90% CI:77.68-120.02) however, median M1 $t_{max}$ was reached earlier (i.e., 58.21 hours versus 109.6 hours).

M2 $AUC_{inf}$ was 15% lower (GMR:84.74; 90% CI:77.13-93.11), while M2 $C_{max}$ was 34% higher (GMR:133.7; 90% CI:118.63-150.76). Median M2 $t_{max}$ was reached earlier (i.e., 71.86 hours versus 167.7 hours).

Sum of enzalutamide plus M2 AUCs was 37% lower (GMR 63.26; 90% CI:58.17-68.79), while $C_{max}$ was similar (GMR:94.32; 90% CI:85.05-104.60). Mean $t_{max}$ values were similar (i.e., 1.039 hours versus 1.078 hours), with comparable ranges of individual values.

Rifampin $C_{2h}$ concentrations indicated that steady-state rifampin exposure was achieved prior to and maintained after administration of enzalutamide on day 8

Example 2. Pharmacodynamics

Data handling. For subject 10037 and subject 10046 in the enzalutamide treatment arm (treatment arm 1), the actual time of urine sampling on day 1 was not within 180 minutes inclusive of enzalutamide dosing and/or pre-dose of rifampin. In addition, for many subjects, urine samples taken post enzalutamide dose were not taken within 180 minutes of the 'virtual' enzalutamide dosing time (i.e., day 1 enzalutamide dosing time [enzalutamide treatment arm{treatment arm 1}] and day 8 enzalutamide dosing time [enzalutamide+rifampin treatment arm {treatment arm 2}]) and/or pre-dose of rifampin. The 6β-hydroxycortisol and cortisol concentrations of these urine samples and obtained 6β-hydroxycortisol/cortisol ratios were excluded from summary statistics.

6β-Hydroxycortisol/Cortisol Ratio for Treatment Arm 1

In treatment arm 1 (enzalutamide alone), the urinary 6β-hydroxycortisol/cortisol ratio increased from a baseline mean value of 6.8±5.1 on day 1 to a maximum value of 8.3±3.6 on day 15, returning to baseline (i.e., 6.2±1.9) on day 22.

6β-Hydroxycortisol/Cortisol Ratio for Treatment Arm 2

In treatment arm 2 (enzalutamide in combination with rifampin), the urinary 6β-hydroxycortisol/cortisol ratio increased from a baseline mean value of 6.9±4.2 on day 1 to 24.2±22.1 on day 8 (the day of enzalutamide administration). From day 8 to day 22 (the end of rifampin administration), mean ratios were variable and ranged between 19.12 and 29.38, returning to baseline (i.e., 6.4±3.2) by day 36.

TABLE 10

Summary Statistics of Urine 6β-hydroxycortisol/Cortisol Ratio After a Single Dose of 160 mg Enzalutamide Alone or in the Presence of Multiple Doses of 600 mg Rifampin Once Daily

| Day | n | Mean | SD | CV % | Min | Max | Median |
|---|---|---|---|---|---|---|---|
| Enzalutamide | | | | | | | |
| 1 | 11 | 6.844 | 5.060 | 73.9 | 1.74 | 17.3 | 5.256 |
| 4 | 11 | 5.760 | 1.840 | 32.0 | 2.51 | 8.11 | 6.390 |
| 8 | 9 | 7.855 | 3.232 | 41.1 | 3.83 | 14.5 | 8.094 |
| 15 | 11 | 8.347 | 3.637 | 43.6 | 4.28 | 14.8 | 6.872 |
| 22 | 9 | 6.204 | 1.892 | 30.5 | 3.71 | 9.31 | 5.647 |
| 29 | 8 | 6.519 | 2.785 | 42.7 | 3.15 | 11.5 | 6.590 |
| 36 | 8 | 8.212 | 5.261 | 64.1 | 2.00 | 19.6 | 7.153 |
| 43 | 8 | 6.576 | 3.062 | 46.6 | 3.13 | 13.1 | 6.294 |
| 50 | 7 | 5.119 | 2.094 | 40.9 | 2.15 | 7.59 | 4.802 |
| Enzalutamide + Rifampin | | | | | | | |
| 1 | 14 | 6.855 | 4.238 | 61.8 | 2.73 | 17.7 | 5.730 |
| 4 | 14 | 19.25 | 14.43 | 75.0 | 6.94 | 65.8 | 14.44 |
| 8 | 14 | 24.23 | 22.12 | 91.3 | 9.16 | 92.2 | 15.98 |
| 11 | 14 | 23.04 | 13.19 | 57.3 | 11.2 | 56.2 | 16.82 |
| 15 | 14 | 19.12 | 8.586 | 44.9 | 8.28 | 41.7 | 17.95 |
| 22 | 14 | 29.38 | 16.64 | 56.6 | 7.26 | 56.4 | 23.42 |
| 29 | 12 | 13.01 | 11.77 | 90.5 | 4.98 | 47.8 | 9.727 |
| 36 | 11 | 6.356 | 3.164 | 49.8 | 4.14 | 15.0 | 5.410 |
| 43 | 10 | 6.216 | 2.581 | 41.5 | 2.58 | 9.86 | 6.486 |
| 50 | 10 | 7.067 | 2.724 | 38.5 | 3.31 | 10.9 | 6.894 |
| 57 | 12 | 6.974 | 2.235 | 32.0 | 2.84 | 10.0 | 7.018 |

CV %: coefficient of variation expressed as percentage;

Max: maximum;

Min: minimum

CONCLUSION

The pharmacodynamic assessment confirmed that rifampin had produced an inductive effect on CYP3A4 by the time that enzalutamide was administered on day 8; whereas, a single dose of enzalutamide alone produced a minimal inductive effect on CYP3A4.

The invention claimed is:

1. A method of treating prostate cancer in a patient to whom rifampin is administered, comprising co-administering to the patient a daily dose of 240 mg enzalutamide.

2. The method of claim 1, wherein the prostate cancer is castration-resistant prostate cancer.

3. The method of claim 1, wherein the prostate cancer is hormone-sensitive prostate cancer.

4. The method of claim 1, wherein the prostate cancer is metastatic prostate cancer.

5. The method of claim 4, wherein the prostate cancer is metastatic castration-resistant prostate cancer.

6. The method of claim 4, wherein the prostate cancer is metastatic hormone-sensitive prostate cancer.

* * * * *